United States Patent
Yamashita et al.

(10) Patent No.: US 12,065,719 B2
(45) Date of Patent: Aug. 20, 2024

(54) Ni—Ti-BASED ALLOY MATERIAL, METHOD FOR PRODUCING Ni—Ti-BASED ALLOY MATERIAL, AND WIRE OR TUBE INCLUDING Ni—Ti-BASED ALLOY MATERIAL

(71) Applicants: FURUKAWA TECHNO MATERIAL CO., LTD., Hiratsuka (JP); FURUKAWA ELECTRIC CO., LTD., Tokyo (JP)

(72) Inventors: Fumiyoshi Yamashita, Hiratsuka (JP); Sumio Kise, Hiratsuka (JP); Kenji Uruma, Hiratsuka (JP)

(73) Assignees: FURUKAWA TECHNO MATERIAL CO., LTD., Hiratsuka (JP); FURUKAWA ELECTRIC CO., LTD., Tokyo (JP)

(*) Notice: Subject to any disclaimer, the term of this patent is extended or adjusted under 35 U.S.C. 154(b) by 113 days.

(21) Appl. No.: 17/614,486

(22) PCT Filed: Apr. 30, 2020

(86) PCT No.: PCT/JP2020/018288
§ 371 (c)(1),
(2) Date: Nov. 26, 2021

(87) PCT Pub. No.: WO2020/241176
PCT Pub. Date: Dec. 3, 2020

(65) Prior Publication Data
US 2022/0220581 A1    Jul. 14, 2022

(30) Foreign Application Priority Data
May 29, 2019 (JP) .................... 2019-100792

(51) Int. Cl.
*C22C 19/03* (2006.01)
*C21D 8/06* (2006.01)
*C21D 8/10* (2006.01)

(52) U.S. Cl.
CPC ............... *C22C 19/03* (2013.01); *C21D 8/06* (2013.01); *C21D 8/10* (2013.01)

(58) Field of Classification Search
CPC ....... C22C 19/00; C22C 19/007; C22C 19/03; C22C 1/023; C22C 1/0433; C22C 14/00; C21D 8/06; C21D 8/10; C22F 1/10
See application file for complete search history.

(56) References Cited

U.S. PATENT DOCUMENTS

| | | |
|---|---|---|
| 2004/0187980 A1 | 9/2004 | Jung et al. |
| 2009/0165898 A1* | 7/2009 | Wong ............... A61L 31/022 623/1.18 |
| 2017/0120344 A1 | 5/2017 | Igarashi |

FOREIGN PATENT DOCUMENTS

| | | | |
|---|---|---|---|
| CN | 103789566 A | | 5/2014 |
| CN | 106457415 A | | 2/2017 |
| CN | 107164653 A | | 9/2017 |
| CN | 107805741 A | | 3/2018 |
| JP | 4-83839 A | | 3/1992 |
| JP | 09118967 A | * | 5/1997 |
| JP | 2001131664 A | * | 5/2001 |
| JP | 2002-182162 A | | 6/2002 |
| JP | 2016-27200 A | | 2/2016 |
| JP | 2016027200 A | * | 2/2016 |

OTHER PUBLICATIONS

International Search Report mailed on Jul. 28, 2020 in PCT/JP2020/018288 filed on Apr. 30, 2020, 2 pages.
Notice of Reasons for Rejection issued on Sep. 17, 2021 in Chinese Patent Application No. 202080004972.1, 10 pages (with English translation).
Hara et al., "Rotating-bending Fatigue Properties of NiTi Wires for Biomedical Applications", Processing and Fabrication of Advanced Materials, XXIV, 2015, pp. 20-28.
Sadrnezhaad et al., "Effect of Microstructure on Rolling Behavior of NiTi Memory Alloy", Materials and Manufacturing Processes, vol. 23, 2008, pp. 646-650, 7 total pages.

* cited by examiner

*Primary Examiner* — Alexandra M Moore
(74) *Attorney, Agent, or Firm* — Oblon, McClelland, Maier & Neustadt, L.L.P.

(57) ABSTRACT

A Ni—Ti-based alloy material includes a matrix phase consisting essentially of a Ni—Ti-based alloy and having a B2 type crystal structure. A nonmetallic inclusion is present in the matrix phase, in which 99% by mass or more of the nonmetallic inclusion is a TiC-based inclusion having a NaCl type crystal structure, the TiC-based inclusion has a lattice misfit ($\delta$) in a range of 0.4238 or more and 0.4259 or less. The lattice misfit ($\delta$) is represented by Expression $\delta=(a1-a2)/a2$, where a1 is a lattice constant (Å) of the TiC-based inclusion and a2 is a lattice constant (Å) of the matrix phase.

14 Claims, 2 Drawing Sheets

Ni—Ti-BASED ALLOY MATERIAL, METHOD FOR PRODUCING Ni—Ti-BASED ALLOY MATERIAL, AND WIRE OR TUBE INCLUDING Ni—Ti-BASED ALLOY MATERIAL

TECHNICAL FIELD

The present disclosure relates to a Ni—Ti-based alloy material, a method for producing a Ni—Ti-based alloy material, and a wire or a tube including Ni—Ti-based alloy material.

BACKGROUND ART

Conventionally, Ni—Ti-based alloy materials are excellent for, for example, corrosion resistance, abrasion resistance, a shape memory property, superelasticity, and resistance to fatigue fracture due to cyclical deformation (hereinafter may be referred to as "fatigue durability") and have been applied in various fields. In recent years, with the advancement of techniques for processing the Ni—Ti-based alloy materials into ultrafine wires or thin-walled capillary tubes, their application has been expanding to medical devices such as stent, artificial heart valve, and guidewires used to insert a stent or a catheter into the body.

Such medical devices require particularly high fatigue durability. Among them, the stent and the artificial heart valve are desired to have excellent fatigue durability over a long period of time of 10 years or longer since the stent and the artificial heart valve experience cyclical loads involving contraction and dilatation in the body due to pulsation of the blood vessels, etc. Therefore, a various researches have been conducted to further improve the fatigue durability of the Ni—Ti-based alloy materials for such applications. Fatigue fracture of the Ni—Ti-based alloy materials has been known to originate from surface defects such as machined flaws on surfaces, void defects in nonmetallic inclusions exposed on surfaces or around the nonmetallic inclusions, or nonmetallic inclusions inside the bulk of alloys. In Non-Patent Document 1, the present inventors investigated which type of the nonmetallic inclusions affect the fatigue fracture of the Ni—Ti-based alloy material, and disclosed that, among the nonmetallic inclusions present in the Ni—Ti-based alloy material, $Ti_4Ni_2O_x$ has a relatively large effect on the fatigue fracture of the Ni—Ti-based alloy material. Furthermore, in Patent Document 1, the present inventors have found that, among the nonmetallic inclusions present in the Ni—Ti-based alloy material, reducing an amount of $Ti_4Ni_2O_x$ is more effective for the above-mentioned fatigue durability, and disclosed is a Ni—Ti-based superelastic alloy material or shape memory alloy material having a carbon concentration [C] of less than 0.05% by mass, an oxygen concentration [O] of less than 0.05% by mass, and a ratio (carbon concentration/oxygen concentration ([C]/[O])) of the carbon concentration to the oxygen concentration of 1.5 or more; including a TiC single phase as a nonmetallic inclusion in the material; and having a fatigue limit of 480 MPa or more. Such a Ni—Ti-based superelastic alloy material or shape memory alloy material allows a Ni—Ti-based alloy material with improved fatigue durability to be produced.

However, in order to control the ratio of the carbon concentration to the oxygen concentration to fall within the above-mentioned range in the Ni—Ti-based alloy material disclosed in Patent Document 1, special raw materials such as expensive ultra-low oxygen-containing titanium which is not distributed at the commercial level had to be obtained, leading to problems from the viewpoints of a procurement cost of the raw materials and mass productivity. Furthermore, in ASTM F2063-18 (Standard Specification for Wrought Nickel-Titanium Shape Memory Alloys for Medical Device and Surgical Implants) which is the standard for Ni—Ti alloys for medical use, allowable carbon and oxygen concentrations were revised to up to 0.04% by mass respectively, in other words, the carbon concentration and the oxygen concentration had to be controlled to an even narrower range than before. Therefore, there is a need to develop a technique that can produce a Ni—Ti-based alloy material with excellent fatigue durability by optimizing other production conditions without controlling the ratio of the carbon concentration to the oxygen concentration.

Patent Document 1: Japanese Unexamined Patent Application, Publication No. 2016-27200

Non-Patent Document 1: Processing and Fabrication of Advanced Materials, XXIV, 2015, p. 20-28

DISCLOSURE OF THE INVENTION

Problems to be Solved by the Invention

The present disclosure has been made in view of the above-described problems. An object of the present disclosure is to provide a Ni—Ti-based alloy material with excellent fatigue durability by optimizing a lattice constant of a nonmetallic inclusion present in a matrix phase relative to a lattice constant of the matrix phase without using expensive ultra-low oxygen-containing titanium as a raw material; a method for producing the Ni—Ti-based alloy material; and a wire or a tube including the Ni—Ti-based alloy material.

Means for Solving the Problems

[1] A Ni—Ti-based alloy material including: a matrix phase consisting essentially of a Ni—Ti-based alloy and having a B2 type crystal structure; and a nonmetallic inclusion present in the matrix phase, in which 99% by mass or more of the nonmetallic inclusion is a TiC-based inclusion having a NaCl type crystal structure, the TiC-based inclusion has a lattice misfit (δ) in a range of 0.4238 or more and 0.4259 or less, the lattice misfit (δ) being represented by Expression (1) below, and a1 is a lattice constant (Å) of the TiC-based inclusion and a2 is a lattice constant (Å) of the matrix phase.

$$\delta = (a1 - a2)/a2 \qquad \text{Expression (1)}$$

[2] The Ni—Ti-based alloy material according to [1], in which 100% by mass of the nonmetallic inclusion is the TiC-based inclusion.

[3] The Ni—Ti-based alloy material according to [1] or [2], the Ni—Ti-based alloy material includes 54.5% by mass or more and 57.0% by mass or less of Ni, 0.04% by mass or less of C, and 0.04% by mass or less of O, with a balance being Ti and unavoidable impurities.

[4] The Ni—Ti-based alloy material according to any one of [1] to [3], the Ni—Ti-based alloy material has a ratio ([C]/[O] ratio) of a carbon concentration ([C]) to an oxygen concentration ([O]) in a range of 0.8 or more and less than 1.5.

[5] The Ni—Ti-based alloy material according to any one of [1] to [4], the Ni—Ti-based alloy material has superelasticity.

[6] A method for producing the Ni—Ti-based alloy material according to any one of [1] to [5], the method including: sequentially subjecting a Ni—Ti-based alloy raw material to at least a melting/casting step (step 1), a hot working step (step 2), a cold working step (step 3), an annealing step (step 4), and a superelasticity-imparting heat treatment step (step 5), in which a Ni—Ti-based alloy ingot obtained in the melting/casting step (step 1) has a carbon concentration ([C]) of 0.04% by mass or less, an oxygen concentration ([O]) of 0.04% by mass or less, and a ratio ([C]/[O] ratio) of the carbon concentration ([C]) to the oxygen concentration ([O]) of 0.5 or more, and the Ni—Ti-based alloy raw material is heated at a temperature of 500° C. or more and 800° C. or less in the hot working step (step 2).

[7] A wire or a tube including the Ni—Ti-based alloy material according to any one of [1] to [5].

[8] A tube for a stent or for an artificial heart valve, the tube being formed of the Ni—Ti-based alloy material according to [5].

[9] A wire for a guidewire, the wire is formed of the Ni—Ti-based alloy material according to [5].

Effects of the Invention

According to the present disclosure, the Ni—Ti-based alloy material with excellent fatigue durability by optimizing the lattice constant of the nonmetallic inclusion present in the matrix phase relative to the lattice constant of the matrix phase without using expensive ultra-low oxygen-containing titanium as a raw material; the method for producing the Ni—Ti-based alloy material; and the wire or the tube including the Ni—Ti-based alloy material can be provided.

Figure 1:
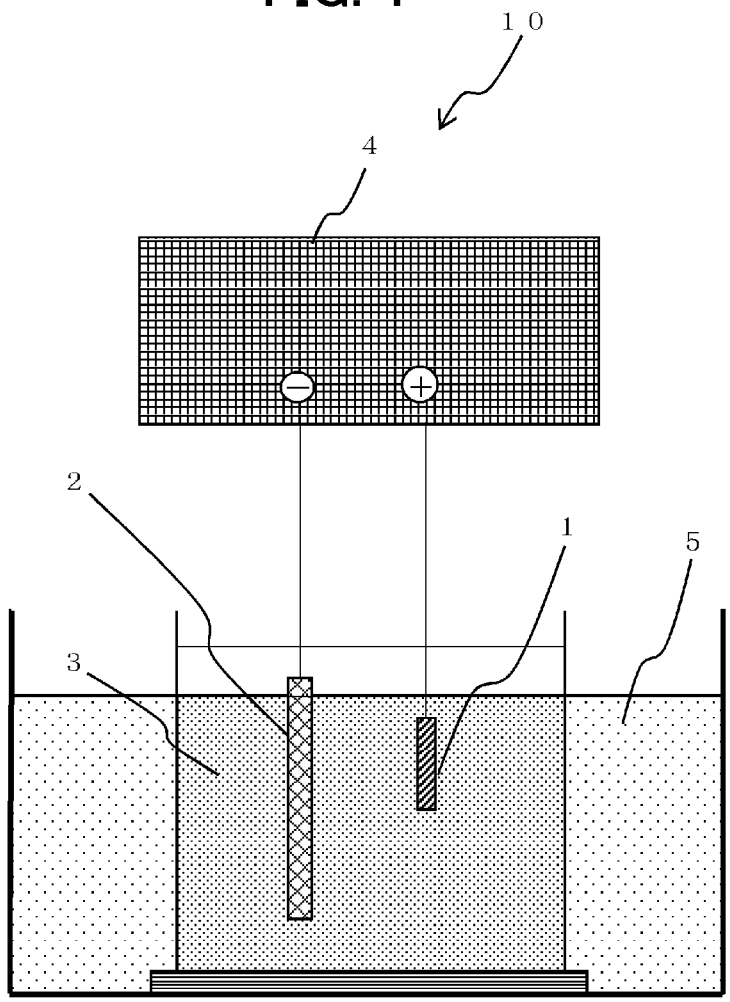
FIG. 1 is a schematic diagram showing an electrolytic extraction apparatus used when a nonmetallic inclusion for X-ray diffraction (XRD) measurement is electrolytically extracted from a sample (specimen) of a Ni—Ti-based alloy material according to an embodiment.

PREFERRED MODE FOR CARRYING OUT
THE INVENTION

Embodiments will now be described in detail. However, the present disclosure is not limited to the following embodiments.

The present inventors have found that fatigue durability of a Ni—Ti-based alloy material is remarkably improved by appropriately controlling 99% by mass or more of a nonmetallic inclusion to a TiC-based inclusion having a NaCl type crystal structure and appropriately controlling a lattice constant of the TiC-based inclusion relative to a lattice constant of a matrix phase consisting essentially of a Ni—Ti-based alloy, without using expensive ultra-low oxygen-containing titanium as a raw material. Thus, the present disclosure has been completed.

First Embodiment (Ni—Ti-based Alloy Material)

A Ni—Ti-based alloy material according to a first embodiment includes a matrix phase consisting essentially of a Ni—Ti-based alloy and having a B2 type crystal structure, and a nonmetallic inclusion present in the matrix phase, in which 99% by mass or more of the nonmetallic inclusion is a TiC-based inclusion having a NaCl type crystal structure, and the TiC-based inclusion has a lattice misfit (δ) in a range of 0.4238 or more and 0.4259 or less represented by Expression (1) below.

$$\delta = (a1 - a2)/a2 \qquad \text{Expression (1)}$$

A1 is a lattice constant (Å) of the TiC-based inclusion and a2 is a lattice constant (Å) of the matrix phase. The above-mentioned Ni—Ti-based alloy material is mainly composed of the matrix phase (matrix) and the nonmetallic inclusion present in the matrix phase. Furthermore, the above-mentioned Ni—Ti-based alloy material preferably has superelasticity. Moreover, the above-mentioned Ni—Ti-based alloy material preferably includes 54.5% by mass or more and 57.0% by mass or less of Ni, 0.04% by mass or less of C, and 0.04% by mass or less of O, with the balance being Ti and unavoidable impurities, in order to achieve the desired processability.

(Ni: 54.5% by Mass or More and 57.0% by Mass or Less)

Ni (nickel) is an element that is needed to allow the Ni—Ti-based alloy material to exert superelasticity or a shape memory property. However, a Ni content out of the range of 54.5% by mass or more and 57.0% by mass or less makes the Ni—Ti-based alloy material difficult to process. Therefore, particularly when the Ni—Ti-based alloy material is used in applications for which processability is important, the Ni content is preferably in a range of 54.5% by mass or more and 57.0% by mass or less, and more preferably in a range of 54.8% by mass or more and 56.5% by mass or less.

(C: 0.04% by Mass or Less)

C (carbon) is an element forming the nonmetallic inclusion. When a C content is higher, the number of the nonmetallic inclusions present in the matrix phase is larger and occupancy of the nonmetallic inclusion in the Ni—Ti-based alloy material (product) is higher, making it easier to cause fatigue fracture. Therefore, the C content is preferably as low as possible. Specifically, the C content is preferably 0.04% by mass or less particularly based on the standard ASTM F2063-18 (Standard Specification for Wrought Nickel-Titanium Shape Memory Alloys for Medical Device and Surgical Implants).

(O: 0.04% by Mass or Less)

O (oxygen) is an element forming the nonmetallic inclusion. When an O content is higher, a particle diameter of the nonmetallic inclusion is larger, making it easier to cause fatigue fracture. Therefore, the O content is preferably as low as possible. Specifically, the O content is preferably 0.04% by mass or less particularly based on the standard ASTM 2063-18.

Note that the Ni—Ti-based alloy material ideally does not include the nonmetallic inclusion in the matrix phase, however, in the present embodiment, it is extremely difficult for the Ni—Ti-based alloy material to include no nonmetallic inclusion in the matrix phase. In light of the above, the present embodiment tries to optimize a type of the nonmetallic inclusion present in the matrix phase of the Ni—Ti-based alloy and the lattice constant of the nonmetallic inclusion (particularly TiC-based inclusion) on the assumption that the nonmetallic inclusion is present in the Ni—Ti-based alloy material.

<Ratio ([C]/[O] ratio) of Carbon Concentration ([C]) to Oxygen Concentration ([O]): 0.8 or More and Less than 1.5>

The ratio ([C]/[O] ratio) of a carbon concentration ([C]) to an oxygen concentration ([O]) of the Ni—Ti-based alloy material according to the present embodiment is preferably 0.8 or more and less than 1.5 and more preferably 0.8 or more and less than 1.4. The [C]/[O] ratio falling within the above-mentioned range can suppress production of a non-TiC-based inclusion (e.g., $Ti_4Ni_2O_x$) that has a relatively large effect on fatigue fracture of the Ni—Ti-based alloy material, and control appropriately the lattice constant of the TiC-based inclusion relative to the lattice constant of the matrix phase (austenite phase) consisting essentially of the Ni—Ti-based alloy to thereby allow a lattice misfit ($\delta$) to fall within the predetermined range and to suppress occurrence of a crack due to cyclical deformation. As a result, fatigue durability (fatigue strength) can be further improved.

(Other Optional Elements)

Moreover, the Ni—Ti-based alloy material according to the present embodiment may include more than 0.00% by mass and 0.05% by mass or less in total of one element or two or more elements selected from the group consisting of Cu (copper), Ta (tantalum), Zr (zirconium), Nb (niobium), V (vanadium), Mo (molybdenum), Cr (chromium), Fe (iron), and Co (cobalt), in order to control the shape memory property or the superelasticity. These elements are added as needed in order to control the shape memory property or the superelasticity. A concentration of each of these elements of 0.05% by mass or less does not affect phases or physical properties of the nonmetallic inclusion. Furthermore, the Ni—Ti-based alloy material according to the present embodiment may include unavoidable impurities. The unavoidable impurities refer to impurities included at a level that may unavoidably contaminate in production steps. For example, 0.005% by mass or less of N may be included as the unavoidable impurities.

<Matrix Phase>

The matrix phase is an austenite phase consisting essentially of the Ni—Ti-based alloy and has a B2 type crystal structure taking a CsCl type body-centered cubic lattice structure. Although a lattice constant a2 of the Ni—Ti-based alloy (matrix phase) having the B2 type crystal structure is 3.010 to 3.020 Å, the lattice constant a2 is considered as 3.015 Å, which is an average value of the above range, from the viewpoint of simplified calculation of the lattice misfit ($\delta$) of the TiC-based inclusion.

<Nonmetallic Inclusion>

In general, a nonmetallic inclusion composed of a TiC-based inclusion mainly including carbide such as TiC and a non-TiC-based inclusion mainly including oxynitride such as $Ti_4Ni_2O_x$ is present in the matrix phase of the Ni—Ti-based alloy material. However, when an amount of the nonmetallic inclusion present in the matrix phase is increased, fatigue fracture originating from the nonmetallic inclusion more easily occurs. Among the inclusions present in the matrix phase, the non-TiC-based inclusion, especially $Ti_4Ni_2O_x$ is particularly likely to act as an origin of the fatigue fracture.

«TiC-based Inclusion»

The TiC-based inclusion included in the Ni—Ti-based alloy material according to the present embodiment has a NaCl type crystal structure. In the present embodiment, a rate of the TiC-based inclusion in the nonmetallic inclusion is 99% by mass or more, so that a content of the non-TiC-based inclusion such as $Ti_4Ni_2O_x$ that is likely to be a fatigue fracture origin can be reduced to thereby suppress formation of the fatigue fracture origin and improve fatigue durability. In the present embodiment, the rate of the TiC-based inclusion in the nonmetallic inclusion is 99% by mass or more, and a lattice constant a1 of the TiC-based inclusion is controlled so that the lattice misfit ($\delta$) calculated from the lattice constant a2 of the matrix phase in the Ni—Ti-based alloy material and the lattice constant a1 of the TiC-based inclusion present in the matrix phase is 0.4238 or more and 0.4259 or less. This makes it less likely to cause a linear defect due to embrittlement of the nonmetallic inclusion, especially the non-TiC-based inclusion to thereby suppress fatigue fracture originating from the linear defect, resulting in remarkable improvement of fatigue durability. Moreover, the rate of the TiC-based inclusion in the nonmetallic inclusion of 100% by mass can further enhance the improvement of fatigue durability. Note that an amount (% by mass) of the TiC-based inclusion in the nonmetallic inclusion present in the matrix phase of the Ni—Ti-based alloy material can be measured using X-ray diffractometry (XRD). The nonmetallic inclusion is measured by extracting a nonmetallic inclusion residue onto a filter with the below-mentioned TiC-based inclusion extraction method and then identifying a nonmetallic inclusion phase with an XRD device. Furthermore, a fraction (% by mass) of the nonmetallic inclusion phase is determined with an RIR (Reference Intensity Ratio) method.

<Calculation Method of Lattice Misfit of TiC-based Inclusion Relative to Matrix Phase of Ni—Ti-based Alloy Material>

1. Extraction Method of Nonmetallic Inclusion Present in Ni—Ti-based Alloy Material FIG. 1 is a schematic diagram showing an electrolytic extraction apparatus used when a nonmetallic inclusion for XRD measurement is electrolytically extracted from a sample (specimen) of a Ni—Ti-based alloy material according to the present embodiment. The electrolytic extraction apparatus 10 includes a specimen of a Ni—Ti-based alloy material 1, a Pt mesh electrode 2 which is a counter electrode against the specimen, an electrolytic solution 3, a direct-current power supply for electrolysis 4, and ice water for cooling (cooling water) 5. First, a commercially available electrolytic solution composed of 10% acetylacetone—1% tetramethylammonium chloride—methyl alcohol is used as the electrolytic solution. Next, this electrolytic solution is injected into the electrolytic extraction apparatus shown in FIG. 1, the specimen of the Ni—Ti-based alloy material (length: 15 mm, wide: 5 mm, thickness: 2 mm) is placed in the predetermined location in the electrolytic extraction apparatus to thereby be immersed into the electrolytic solution, and then, the Ni—Ti-based alloy material is eluted into the electrolytic solution by applying a voltage of 4 V to the specimen. Subsequently, the electrolytic solution into which the Ni—Ti-based alloy material has been eluted is centrifuged with a centrifugal separator and then is subjected to suction filtration with a membrane filter having a pore diameter of 0.2 μm to separate the nonmetallic inclusion (particle) in the electrolytic solution as a residue. Thus, nonmetallic inclusion particles can be extracted (collected).

2. Calculation Method of Lattice Constant of TiC-based Inclusion

The thus-obtained nonmetallic inclusion is subjected to XRD measurement, a spacing (d) of a peak on a surface (200) of TiC is determined from the resultant X-ray diffraction spectra, and the lattice constant a1 can be calculated from the following expression: $d = a1/\sqrt{(h^2+k^2+l^2)}$ (a1: lattice constant, h, k, l: Miller index). Note that since the nonmetallic inclusion includes 99% by mass or more of the TiC-based inclusion, in the present embodiment, the thus-calculated lattice constant a1 is considered as a lattice constant of the TiC-based inclusion.

3. Calculation Method of Lattice Misfit

The thus-calculated lattice constant a1 of the TiC-based inclusion and the lattice constant a2 (3.015 Å) of the matrix phase in the Ni—Ti-based alloy material can be assigned to Expression (1) below to thereby calculate a lattice misfit (δ) which is a value obtained by dividing a difference between the lattice constant of the TiC-based inclusion and the lattice constant of the matrix phase in the Ni—Ti-based alloy material by the lattice constant of the matrix phase in the Ni—Ti-based alloy material.

$$\delta = (a1 - a2)/a2 \qquad \text{Expression (1)}$$

The lattice misfit (δ) of 0.4238 or more and 0.4259 or less improves matching between the TiC-based inclusion and the matrix phase in the Ni—Ti-based alloy material to thereby suppress the formation of fatigue fracture origin particularly on an interface between the TiC-based inclusion and the matrix phase in the Ni—Ti-based alloy material, resulting in improvement of fatigue durability. Moreover, the lattice misfit (δ) of 0.4238 to 0.4255 is preferable since the improvement of fatigue durability is further enhanced. The lattice misfit (δ) of the TiC-based inclusion relative to the matrix phase can be controlled by controlling the lattice constant of the TiC-based inclusion, for example, as mentioned below.

<Control Method of Lattice Constant of TiC-based Inclusion>

The lattice constant of the TiC-based inclusion can be controlled by, for example, replacing, with oxygen atoms, some of the carbon atoms at a lattice position in the NaCl type crystal structure that the TiC-based inclusion has. Such replacement between different kinds of atoms can be performed by, for example, appropriately controlling conditions (e.g., cooling rate upon casting) of a melting/casting step (step 1) in the below-mentioned production method of Ni—Ti-based alloy material.

Second Embodiment (Production Method of Ni—Ti-based Alloy Material)

A method for producing a Ni—Ti-based alloy material according to a second embodiment includes sequentially subjecting a Ni—Ti-based alloy raw material to at least a melting/casting step (step 1), a hot working step (step 2), a cold working step (step 3), an annealing step (step 4), and a superelasticity-imparting heat treatment step (step 5), in which a Ni—Ti-based alloy ingot obtained in the melting/casting step (step 1) has a carbon concentration ([C]) of 0.04% by mass or less, an oxygen concentration ([O]) of 0.04% by mass or less, and a ratio ([C]/[O] ratio) of the carbon concentration ([C]) to the oxygen concentration ([O]) of 0.5 or more, and the Ni—Ti-based alloy raw material is heated at a temperature of 500° C. or more and 800° C. or less in the hot working step (step 2).

<Melting/Casting Step (Step 1)>

The melting/casting step (step 1) is a step of melting a Ni—Ti-based alloy raw material and then casting it to thereby produce a Ni—Ti-based alloy ingot, and the thus-produced ingot is controlled so as to have the carbon concentration ([C]) of 0.04% by mass or less, the oxygen concentration ([O]) of 0.04% by mass or less, and the [C]/[O] ratio of 0.5 or more. When both the carbon concentration ([C]) and the oxygen concentration ([O]) in the Ni—Ti-based alloy ingot obtained in the step 1 are 0.04% by mass or less, the ingot can satisfy conditions specified in ASTM F2063-18 (Standard Specification for Wrought Nickel-Titanium Shape Memory Alloys for Medical Device and Surgical Implants) which is the standard for Ni—Ti alloys for medical use, and can be applied for medical use mentioned below. Furthermore, the [C]/[O] ratio of 0.5 or more can suppress $Ti_4Ni_2O_x$ from forming in the ingot obtained in the step 1 to thereby improve fatigue durability. Additionally, controlling the [C]/[O] ratio of 0.5 or more in the melting/casting step (step 1) is preferable since the ratio ([C]/[O] ratio) of a carbon concentration ([C]) to an oxygen concentration ([O]) in the Ni—Ti-based alloy material can be more easily controlled to a range of 0.8 or more and less than 1.5.

The above-mentioned Ni—Ti-based alloy raw material can be melted using a high-frequency melting method under a vacuum atmosphere or an inert gas atmosphere such as an Ar gas.

In the present embodiment, the carbon concentration (% by mass) and the oxygen concentration (% by mass) in the melting/casting step are controlled as follows. The carbon concentration (% by mass) in the case of the above-mentioned high-frequency melting furnace is controlled by weighing a carbon amount so that a total carbon amount involving an additional carbon amount to be eluted from a crucible to be used is the predetermined amount. The oxygen concentration (% by mass) is controlled by selecting a grade of titanium metal and weighing the titanium metal so that an oxygen amount is the predetermined amount based on the fact that an oxygen amount included in the titanium metal serving as a raw material varies depending on the grade.

Note that the carbon concentration and the oxygen concentration can be measured with a conventionally known carbon analyzer and oxygen analyzer, respectively.

(Control of Cooling Rate upon Casting)

In the present embodiment, upon controlling the lattice misfit (δ), which is a value obtained by dividing a difference between the lattice constant of the TiC-based inclusion and the lattice constant of the matrix phase in the Ni—Ti-based alloy material by the lattice constant of the matrix phase in the Ni—Ti-based alloy material, to 0.4238 to 0.4259, when a cooling rate upon casting in the step 1 is increased, carbon atoms constituting the TiC-based inclusion tend to be more easily replaced with oxygen atoms. Therefore, a process for increasing the cooling rate may be used to control the lattice constant of the TiC-based inclusion to thereby control the lattice misfit (δ) to fall within the range of 0.4238 or more and 0.4259 or less. Note that, in the present embodiment, a method for controlling the lattice misfit (δ) of the TiC-based inclusion relative to the matrix phase to 0.4238 to 0.4259 is not limited to the above-mentioned process. For example, a site of the carbon atom may be replaced with the oxygen atom by supplying an oxygen dopant to the TiC-based inclusion via ion injection.

<Hot Working Step (Step 2)>

The hot working step (step 2) includes a forging step (step 2-1) and a rolling step (step 2-2-1) in the case of producing a wire and includes a forging step (step 2-1) and an extrusion step (step 2-2-2) in the case of producing a tube.

«Forging Step (Step 2-1)»

The forging step (step 2-1) is a step of forging the ingot obtained in the above-mentioned step (step 1) to thereby produce a Ni—Ti-based alloy forged material (may be referred to as Ni—Ti-based alloy hot-worked material), and a heating temperature when the Ni—Ti-based alloy ingot is forged in the (step 2-1) is controlled to 500° C. or more and 800° C. or less and preferably 600° C. or more and 800° C.

or less. This allows 100% by mass of the nonmetallic inclusion present in the matrix phase of the Ni—Ti-based alloy material to be the TiC-based inclusion even at such a relatively low heating temperature and such a relatively low value of the [C]/[O] ratio of 0.8 or more and less than 1.5, making it possible to improve fatigue durability of the Ni—Ti-based alloy material. In the above-mentioned forging step, press forging or air hammer forging may be used.

«Rolling Step (Step 2-2-1) or Extrusion Step (Step 2-2-2)»

The rolling step (step 2-2-1) or the extrusion step (step 2-2-2) is a step of rolling in the case of producing a wire or of extruding in the case of producing a tube against the Ni—Ti-based alloy forged material obtained in the above-mentioned step (step 2-1) to thereby produce a wire or a tube made of the Ni—Ti-based alloy (both are Ni—Ti-based alloy hot-worked material), and a heating temperature when the Ni—Ti-based alloy forged material or the alloy ingot is rolled or extruded in the (step 2-1) is controlled to 500° C. or more and 800° C. or less and preferably 600° C. or more and 800° C. or less. This allows 99% by mass or more, preferably 100% by mass of the nonmetallic inclusion present in the matrix phase of the Ni—Ti-based alloy material to be the TiC-based inclusion even at such a relatively low temperature and such a relatively low value of the [C]/[O] ratio of 0.8 or more and less than 1.5, making it possible to improve the fatigue durability of the Ni—Ti-based alloy material.

<Cold Working Step (Step 3)>

The cold working step (step 3) is a step of cold working the Ni—Ti-based alloy hot-worked material obtained in the hot working step (step 2) to thereby produce a Ni—Ti-based alloy cold-worked material, and includes a cold wire-drawing step (step 3-1) in the case of producing a wire or a drawing step (step 3-2) in the case of producing a tube. In the present embodiment, a wire having a diameter of 20 μm to 3 mm may be produced in the cold working step to thereby produce a tube such as a tube for a stent or for an artificial heart valve or a wire such as a wire for a guidewire as mentioned below. In the cold working step, a heating temperature when the tube or the wire is produced is controlled to 500° C. or more and 800° C. or less and preferably 600° C. or more and 800° C. or less.

<Annealing Step (Step 4)>

The annealing step (step 4) is a step of annealing during the cold working step (step 3) or after the cold working step (step 3) to thereby produce a Ni—Ti-based alloy annealed material in order to remove strain due to working such as wire drawing or drawing in the cold working step (step 3) to recover. In the annealing step (step 4), a heating temperature is controlled to 800° C. or less.

<Superelasticity-imparting Heat Treatment Step (Step 5)>

The superelasticity-imparting heat treatment step (step 5) is a step of allowing the Ni—Ti-based alloy annealed material obtained in the annealing step (step 4) to exert superelasticity to thereby produce a Ni—Ti-based alloy material. The atmosphere or temperature condition when the Ni—Ti-based alloy annealed material is heated in the superelasticity-imparting heat treatment step is not limited. For example, when the Ni—Ti-based alloy annealed material is heated at a temperature of 600° C. or less under an inert gas atmosphere, an amount of $Ti_4Ni_2O_x$ in the nonmetallic inclusion present in a Ni—Ti-based alloy material can be reduced to obtain the Ni—Ti-based alloy material with improved fatigue durability.

Third Embodiment (Applications of Ni—Ti-based Alloy Material According to the Present Disclosure)

A third embodiment is a wire or a tube formed of the above-mentioned Ni—Ti-based alloy material. Particularly, the Ni—Ti-based alloy material with superelasticity can be applied to, for example, a tube used for forming medical devices such as a stent or an artificial heart valve or a wire used for forming a guidewire to insert a stent or a catheter into the body, and is expected to be widely used for applications requiring high fatigue durability. Note that the wire as used herein includes not only a round wire but also a flat wire (suitably having an aspect ratio of 2 or less).

EXAMPLES

Examples and Comparative Examples will now be described, but the present disclosure is not limited to these Examples. Note that composition (I by mass) of each of components presented below was determined by the above-mentioned RIR method.

Examples 1 to 11 and Comparative Examples 1 to 16

Table 1 describes compositions (% by mass) of Ni and Ti in Ni—Ti-based alloy materials of Examples 1 to 11 and Comparative Examples 1 to 16 and Table 2 describes production conditions in a melting/casting step (step 1), a forging step (step 2-1), and a rolling step (step 2-2) when the Ni—Ti-based alloy materials were produced. Ni—Ti-based alloy material samples (wire) of Examples 1 to 11 and Comparative Examples 1 to 16 were produced as follows.

TABLE 1

| Sample No. | | Composition (% by mass) | | | | [C]/[O] ratio |
|---|---|---|---|---|---|---|
| | | Ni | Ti | C | O | |
| Example | 1 | 56.1 | balance | 0.029 | 0.036 | 0.8 |
| | 2 | 56.0 | balance | 0.027 | 0.030 | 0.9 |
| | 3 | 56.1 | balance | 0.032 | 0.029 | 1.1 |
| | 4 | 56.0 | balance | 0.035 | 0.028 | 1.3 |
| | 5 | 55.9 | balance | 0.035 | 0.025 | 1.4 |
| | 6 | 55.0 | balance | 0.035 | 0.037 | 0.9 |
| | 7 | 56.0 | balance | 0.031 | 0.027 | 1.1 |
| | 8 | 56.2 | balance | 0.030 | 0.025 | 1.2 |
| | 9 | 56.7 | balance | 0.025 | 0.026 | 1.0 |
| | 10 | 56.1 | balance | 0.030 | 0.036 | 0.8 |
| | 11 | 55.0 | balance | 0.032 | 0.024 | 1.3 |
| Comparative Example | 1 | 56.1 | balance | 0.047 | 0.023 | 2.0 |
| | 2 | 55.8 | balance | 0.025 | 0.042 | 0.6 |
| | 3 | 56.0 | balance | 0.021 | 0.028 | 0.8 |
| | 4 | 55.0 | balance | 0.030 | 0.023 | 1.3 |
| | 5 | 56.1 | balance | 0.035 | 0.045 | 0.8 |
| | 6 | 55.9 | balance | 0.025 | 0.041 | 0.6 |
| | 7 | 56.0 | balance | 0.049 | 0.033 | 1.5 |
| | 8 | 55.9 | balance | 0.025 | 0.060 | 0.4 |
| | 9 | 56.1 | balance | 0.015 | 0.035 | 0.4 |
| | 10 | 56.1 | balance | 0.003 | 0.011 | 0.3 |
| | 11 | 55.5 | balance | 0.025 | 0.042 | 0.6 |
| | 12 | 55.7 | balance | 0.025 | 0.032 | 0.8 |
| | 13 | 56.1 | balance | 0.045 | 0.029 | 1.6 |
| | 14 | 56.0 | balance | 0.032 | 0.029 | 1.3 |
| | 15 | 54.3 | balance | 0.025 | 0.035 | 0.7 |
| | 16 | 57.2 | balance | 0.045 | 0.030 | 1.5 |

TABLE 2

| | | Production conditions | | | | | |
|---|---|---|---|---|---|---|---|
| | | melting/casting step | | | | forging step | rolling step |
| Sample No. | | carbon concentration (% by mass) | oxygen concentration (% by mass) | carbon concentration/oxygen concentration | thermoconductivity of template (W/(m · K)) | heating temperature (° C.) | heating temperature (° C.) |
| Example | 1 | 0.029 | 0.036 | 0.8 | 48 | 700 | 700 |
| | 2 | 0.027 | 0.030 | 0.9 | 48 | 750 | 740 |
| | 3 | 0.032 | 0.029 | 1.1 | 48 | 700 | 750 |
| | 4 | 0.035 | 0.028 | 1.3 | 48 | 750 | 720 |
| | 5 | 0.035 | 0.025 | 1.4 | 48 | 700 | 750 |
| | 6 | 0.035 | 0.037 | 0.9 | 48 | 500 | 750 |
| | 7 | 0.031 | 0.027 | 1.1 | 48 | 700 | 750 |
| | 8 | 0.030 | 0.025 | 1.2 | 48 | 700 | 750 |
| | 9 | 0.025 | 0.026 | 1.0 | 48 | 600 | 780 |
| | 10 | 0.030 | 0.036 | 0.8 | 374 | 700 | 700 |
| | 11 | 0.032 | 0.024 | 1.3 | 374 | 700 | 700 |
| Comparative Example | 1 | 0.047 | 0.023 | 2.0 | 48 | 700 | 790 |
| | 2 | 0.025 | 0.042 | 0.6 | 48 | 600 | 780 |
| | 3 | 0.021 | 0.028 | 0.8 | 1 | 700 | 750 |
| | 4 | 0.030 | 0.023 | 1.3 | 1 | 700 | 750 |
| | 5 | 0.035 | 0.045 | 0.8 | 48 | 800 | 790 |
| | 6 | 0.025 | 0.041 | 0.6 | 48 | 800 | 780 |
| | 7 | 0.049 | 0.033 | 1.5 | 48 | 750 | 780 |
| | 8 | 0.025 | 0.060 | 0.4 | 48 | 800 | 780 |
| | 9 | 0.015 | 0.035 | 0.4 | 48 | 750 | 780 |
| | 10 | 0.003 | 0.011 | 0.3 | 48 | 750 | 780 |
| | 11 | 0.025 | 0.042 | 0.6 | 48 | 450(* 1) | —(* 1) |
| | 12 | 0.025 | 0.032 | 0.8 | 48 | 850 | 780 |
| | 13 | 0.045 | 0.029 | 1.6 | 48 | 750 | 480(* 1) |
| | 14 | 0.032 | 0.029 | 1.3 | 48 | 750 | 900 |
| | 15 | 0.025 | 0.035 | 0.7 | 48 | 750(* 1) | —(* 1) |
| | 16 | 0.045 | 0.030 | 1.5 | 48 | 750(* 1) | —(* 1) |

(* 1): those for which area reduction working or rolling could not be performed

Ni metal and Ti metal, as Ni—Ti-based alloy raw materials and serving as raw materials, were weighed so as to satisfy each of the compositions presented in Table 1 and then charged into a high-frequency melting furnace. At that time, the carbon concentration (% by mass) and the oxygen concentration (% by mass) in the melting/casting step presented in Table 2 were controlled as follows. The carbon concentration (% by mass) in the case of the high-frequency melting furnace was controlled by weighing a carbon amount so that a total carbon amount involving an additional carbon amount to be eluted from a crucible to be used was the predetermined amount. The oxygen concentration (% by mass) was controlled by selecting a grade of titanium metal and weighing the titanium metal so that an oxygen amount is the predetermined amount based on the fact that an oxygen amount included in the titanium metal serving as a raw material varies depending on the grade. Note that the carbon concentration and the oxygen concentration of each of the samples of Examples 1 to 11 and Comparative Examples 1 to 16 presented in Table 2 are measurement values obtained by measuring each Ni—Ti-based alloy ingot with a carbon concentration analyzer and an oxygen concentration analyzer, respectively. Then, a molten metal obtained by melting Ni and Ti in the high-frequency melting furnace was poured into a template having the thermoconductivity presented in the melting/casting step of Table 2 (thermoconductivity for a template made of a cast: 48 W/(m·K), thermoconductivity for a template made of copper: 374 W/(m·K), and thermoconductivity for a template made of a ceramic: 1.0 W/(m·K)) to thereby produce an ingot.

The reason why the lattice misfit was 0.4238 or more and 0.4259 or less is thought to be as follows. Examples 1 to 11 used the template having high thermoconductivity, so that a cooling rate upon casting was increased and thus replacement of carbon atoms constituting the TiC-based inclusion with oxygen atoms was promoted.

Subsequently, the resultant ingot was subjected to area reduction working at the heating temperature in the forging step presented in Table 2 to thereby obtain a forged material. Thereafter, this forged material was subjected to rolling at the heating temperature in the rolling step presented in Table 2 to thereby obtain a hot-worked material. Subsequently, this hot-worked material was subjected to cold working to thereby obtain wire materials. Subsequently, the wire materials were subjected to an annealing treatment in the annealing step to thereby obtain wires each having a diameter of 0.5 mm. Thereafter, the wires were tied together at both ends and were charged into a furnace under an inert gas atmosphere at 500° C. and subjected to a superelasticity-imparting heat treatment to thereby obtain wires with the desired superelasticity made of the Ni—Ti-based alloy material (diameter: 0.5 mm) (sample of each of Examples 1 to 11 and Comparative Examples 1 to 16). Note that, in Table 2, for Comparative Example 11, the area reduction working could not be appropriately performed due to the low heating temperature of 450° C. in the forging step; for Comparative Example 13, the rolling could not be appropriately performed due to the low heating temperature of 480° C. in the rolling step; for Comparative Example 15, a material crack occurred in the forging step and the rolling could not be performed in the rolling step due to the Ni concentration of 54.3% which was lower than the appropriate range; and for Comparative Example 16, a forging crack occurred due to the Ni concentration of 57.2% which was higher than the appropriate range.

(Production of Samples of Examples 12 to 21 and Comparative Examples 17 to 26)

Table 3 describes compositions (% by mass) of Ni—Ti-based alloy material samples (wire) of Examples 12 to 21 and Comparative Examples 17 to 26 and Table 4 describes production conditions in a melting/casting step, a forging step, and a rolling step when the Ni—Ti-based alloy materials were produced. The Ni—Ti-based alloy material samples (wire) of Examples 12 to 21 and Comparative Examples 17 to 26 were produced in the same manner as in Examples 1 to 11 and Comparative Examples 1 to 16, except that one element (Examples 12 to 20 and Comparative Example 17 to 25) or two elements (Example 21 and Comparative Example 26) selected from the group consisting of Cu, Ta, Zr, Nb, V, Mo, Cr, Fe, and Co were further added as a raw material. Note that the carbon concentration and the oxygen concentration of each of the samples of Examples 12 to 21 and Comparative Examples 17 to 26 presented in Table 4 are measurement values obtained by measuring each Ni—Ti-based alloy ingot with a carbon concentration analyzer and an oxygen concentration analyzer, respectively.

TABLE 3

| Sample No. | | Composition (% by mass) | | | | | | | | | | | | [C]/[O] ratio |
|---|---|---|---|---|---|---|---|---|---|---|---|---|---|---|
| | | Ni | Ti | Cu | Ta | Zr | Nb | V | Mo | Cr | Fe | Co | C | O | |
| Example | 12 | 56.2 | balance | 0.05 | — | — | — | — | — | — | — | — | 0.029 | 0.033 | 0.9 |
| | 13 | 56.1 | balance | — | 0.05 | — | — | — | — | — | — | — | 0.027 | 0.034 | 0.8 |
| | 14 | 56.1 | balance | — | — | 0.05 | — | — | — | — | — | — | 0.028 | 0.030 | 0.9 |
| | 15 | 56.2 | balance | — | — | — | 0.05 | — | — | — | — | — | 0.026 | 0.028 | 0.9 |
| | 16 | 56.1 | balance | — | — | — | — | 0.05 | — | — | — | — | 0.023 | 0.025 | 0.9 |
| | 17 | 56.1 | balance | — | — | — | — | — | 0.05 | — | — | — | 0.028 | 0.037 | 0.8 |
| | 18 | 56.1 | balance | — | — | — | — | — | — | 0.05 | — | — | 0.029 | 0.032 | 0.9 |
| | 19 | 56.2 | balance | — | — | — | — | — | — | — | 0.05 | — | 0.029 | 0.032 | 0.9 |
| | 20 | 56.1 | balance | — | — | — | — | — | — | — | — | 0.05 | 0.025 | 0.031 | 0.8 |
| | 21 | 56.1 | balance | 0.01 | — | — | — | — | — | 0.02 | — | — | 0.030 | 0.036 | 0.8 |
| Comparative | 17 | 56.1 | balance | 0.10 | — | — | — | — | — | — | — | — | 0.029 | 0.041 | 0.7 |
| Example | 18 | 56.1 | balance | — | 0.10 | — | — | — | — | — | — | — | 0.045 | 0.030 | 1.5 |
| | 19 | 56.1 | balance | — | — | 0.10 | — | — | — | — | — | — | 0.025 | 0.043 | 0.6 |
| | 20 | 56.2 | balance | — | — | — | 0.10 | — | — | — | — | — | 0.030 | 0.043 | 0.7 |
| | 21 | 56.1 | balance | — | — | — | — | 0.10 | — | — | — | — | 0.028 | 0.050 | 0.6 |
| | 22 | 56.1 | balance | — | — | — | — | — | 0.10 | — | — | — | 0.028 | 0.045 | 0.6 |
| | 23 | 56.1 | balance | — | — | — | — | — | — | 0.10 | — | — | 0.035 | 0.042 | 0.8 |
| | 24 | 56.2 | balance | — | — | — | — | — | — | — | 0.10 | — | 0.035 | 0.042 | 0.8 |
| | 25 | 56.1 | balance | — | — | — | — | — | — | — | — | 0.10 | 0.041 | 0.045 | 0.9 |
| | 26 | 56.1 | balance | 0.05 | — | — | — | — | — | 0.05 | — | — | 0.045 | 0.036 | 1.3 |

TABLE 4

| | | Production conditions | | | | | |
|---|---|---|---|---|---|---|---|
| | | melting/casting step | | | | forging step temperature (° C.) | rolling step temperature (° C.) |
| Sample No. | | carbon concentration (% by mass) | oxygen concentration (% by mass) | carbon concentration/oxygen concentration | thermoconductivity of template (W/(m · K)) | | |
| Example | 12 | 0.029 | 0.033 | 0.9 | 48 | 700 | 750 |
| | 13 | 0.027 | 0.034 | 0.8 | 48 | 700 | 750 |
| | 14 | 0.028 | 0.030 | 0.9 | 48 | 700 | 750 |
| | 15 | 0.026 | 0.028 | 0.9 | 48 | 700 | 750 |
| | 16 | 0.023 | 0.025 | 0.9 | 48 | 700 | 750 |
| | 17 | 0.028 | 0.037 | 0.8 | 48 | 700 | 750 |
| | 18 | 0.029 | 0.032 | 0.9 | 48 | 700 | 750 |
| | 19 | 0.029 | 0.032 | 0.9 | 48 | 700 | 750 |
| | 20 | 0.025 | 0.031 | 0.8 | 48 | 700 | 750 |
| | 21 | 0.030 | 0.036 | 0.8 | 48 | 700 | 750 |
| Comparative | 17 | 0.029 | 0.041 | 0.7 | 48 | 700 | 750 |
| Example | 18 | 0.045 | 0.030 | 1.5 | 48 | 700 | 750 |
| | 19 | 0.025 | 0.043 | 0.6 | 48 | 700 | 750 |
| | 20 | 0.030 | 0.043 | 0.7 | 48 | 700 | 750 |
| | 21 | 0.028 | 0.050 | 0.6 | 48 | 700 | 750 |
| | 22 | 0.028 | 0.045 | 0.6 | 48 | 700 | 750 |
| | 23 | 0.035 | 0.042 | 0.8 | 48 | 700 | 750 |
| | 24 | 0.035 | 0.042 | 0.8 | 48 | 700 | 750 |
| | 25 | 0.041 | 0.045 | 0.9 | 48 | 700 | 750 |
| | 26 | 0.045 | 0.036 | 1.3 | 48 | 700 | 750 |

<Performance Evaluation>

As for performance evaluation of Examples 1 to 21 and Comparative Examples 1 to 26, a lattice misfit (δ) of the TiC-based inclusion in the nonmetallic inclusion present in the matrix phase of each of the samples was calculated and each of the samples was subjected to a rotating bending fatigue test. Furthermore, Examples 1 to 11 and Comparative Examples 1 to 16 were measured for an Af point, that is, a transformation temperature at which a phase conversion from a martensite phase to an austenite phase in the sample ended.

(Calculation of Lattice Misfit)

1. Electrolytic Extraction of TiC-based Inclusion

The TiC-based inclusion was eluted from each of samples of Examples 1 to 21 and Comparative Examples 1 to 26 into an electrolytic solution using the electrolytic extraction apparatus shown in FIG. 1. Thereafter, the resultant effluent of the nonmetallic inclusion was aggregated with a centrifugal separator and then was subjected to suction filtration with a membrane filter having a pore diameter of 0.2 μm to thereby obtain a particulate solid.

2. X-ray Diffraction (XRD) Measurement of TiC-based Inclusion

The thus-obtained TiC-based inclusion was subjected to XRD measurement, a spacing (d) of a peak on a surface (200) of TiC was determined from the resultant XRD spectra, and a lattice constant a1 of the TiC-based inclusion was calculated from the following expression: $d=a1/\sqrt{(h^2+k^2+l^2)}$ (a1: lattice constant of TiC-based inclusion, h, k, l: Miller index). This lattice constant a1 of the TiC-based inclusion and the lattice constant a2 (3.015 Å) of the matrix phase in the Ni—Ti-based alloy material were assigned to Expression (1) below to thereby calculate the lattice misfit (δ) of the TiC-based inclusion relative to the matrix phase in the Ni—Ti-based alloy material.

$$\delta = (a1 - a2)/a2 \quad \text{Expression (1)}$$

Note that the above-mentioned a2 was obtained with reference to the following non-patent document that is Materials and Manufacturing Processes, 23: 646-650, 2008.

(Measurement of Transformation Temperature (Af Point))

The transformation temperature (Af point) (Table 5) of each of the samples of Examples 1 to 11 and Comparative Example 1 to 16 presented in Tables 1 and 2 was a temperature at which reverse transformation from a martensite phase to an austenite phase upon heating ended and measured by Differential Scanning calorimetry (DSC) according to JIS H7101: Method for determining the transformation temperature of shape memory alloys.

(Evaluation of Fatigue Property)

Figure 2:
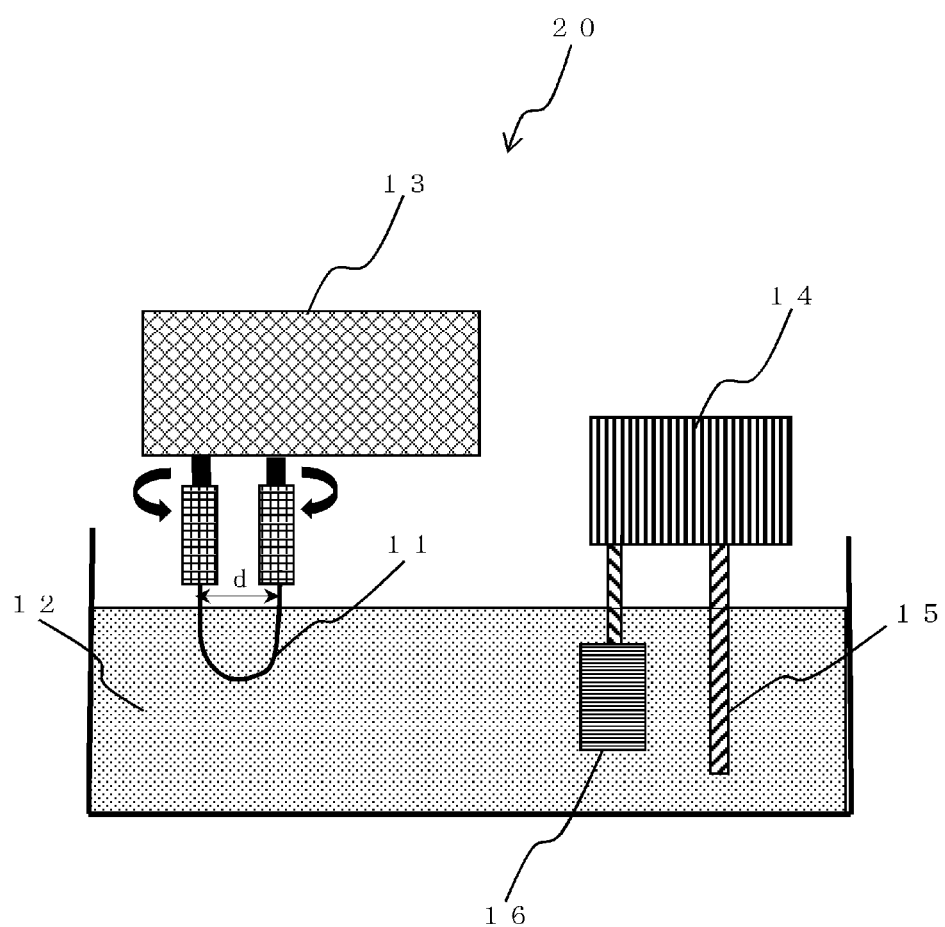
FIG. 2 is a schematic diagram showing a dual-drive type rotating bending fatigue tester to be used to evaluate fatigue durability of a wire made of a Ni—Ti-based alloy material according to an embodiment.

Each of the samples (diameter: 0.5 mm) of Examples 1 to 21 and Comparative Examples 1 to 26 presented in Tables 1 to 4 was subjected to a cyclical deformation fatigue test using a dual-drive type rotating bending fatigue tester 20 equipped with a motor with a revolution counter (counter) 13 and a power supply for a heater with a motor for a stirrer 14 as shown in FIG. 2. Note that the maximum bending stress loaded to a wire made of a Ni—Ti-based alloy material (sample) 11 was varied by controlling a chuck-to-chuck distance d of the wire 11 between 40 and 100 mm using the motor with a revolution counter (counter) 13 and varying a length of the wire 11 between 100 and 200 mm. At that time, the number of revolutions of the wire 11 was 500 revolutions/min. In FIG. 2, a temperature of silicone oil 12 was controlled with a heater 15 and a stirrer 16 using the power supply for a heater with a motor for a stirrer 14 and a bent portion of the wire made of a Ni—Ti-based alloy material (sample) 11 was immersed in the silicone oil 12 which was set to the Af point of the sample. The number of tests (cumulative number of revolutions) was up to $10^7$ times.

Since the evaluation of the fatigue property is affected by physical conditions (roughness, void, defect, etc.) on a surface of the sample, a wire having a final shape of a diameter of 0.5 mm was subjected to electropolishing for 20 seconds by applying a voltage of 15 V in an electrolytic solution which was a mixed solution of 300 mL of methanol and 3 mol of sulfuric acid, to thereby remove a surface defect. An S-N curve for each of the samples was calculated and the stress at which the stress and the number of rotating bendings converged to a nearly constant value was determined as a fatigue strength (MPa). Note that the evaluation of the wire was substituted for evaluation of a tube in the fatigue test since, unlike the wire, a defect and the like on an inner surface of the tube is difficult to remove by polishing, and this affects the fatigue property to make it difficult to clearly evaluate the fatigue property due to the nonmetallic inclusion.

<Evaluation results>

Values of properties of each of the samples of Examples 1 to 11 and Comparative Example 1 to 16, that is, the lattice misfit, the transformation temperature (Af point) (° C.), and the fatigue strength (MPa) are presented in Table 5. As shown in Table 5, for all Examples 1 to 11, 99% by mass or more or 100% by mass of the nonmetallic inclusion was the TiC-based inclusion and the lattice misfit, which was a value obtained by dividing a difference between the lattice constant of the TiC-based inclusion and the lattice constant of the matrix phase in the Ni—Ti-based alloy material by the lattice constant of the matrix phase in the Ni—Ti-based alloy material, was 0.4238 or more and 0.4259 or less. In other words, Examples 1 to 11 conform to the composition of the present application. Therefore, Examples 1 to 11 had fatigue strength in a range of 513 to 540 MPa and excellent fatigue durability. Furthermore, Examples 1 to 11 were found to have a relatively wide range of Af point of −21 to 55° C. This indicates that the wire or the tube of which the desired Af can be set to a relatively wide range can be provided in the present disclosure.

Meanwhile, for Comparative Examples 1 to 4, 7, 11, 13, and 16, 99% by mass or more of the nonmetallic inclusion was the TiC-based inclusion, but the lattice misfit was 0.4232 (Comparative Examples 2, 6, and 11) or 0.4262 to 0.4296 (Comparative Examples 1, 3, 4, 7, 13, and 16) which was out of the appropriate range of the present disclosure. Furthermore, for Comparative Examples 5 and 12, the lattice misfit was 0.4238 for both, but the concentration of the TiC-based inclusion in the nonmetallic inclusion were 98.2% by mass and 98.3% by mass, respectively. For Comparative Examples 8, 9, 14, and 15, the concentration of the TiC-based inclusion in the nonmetallic inclusion was 60 to 98.2% by mass which was out of the appropriate range of the present disclosure. For Comparative Example 10, the concentration of the TiC-based inclusion in the nonmetallic inclusion was 0% by mass. In other words, all Comparative Examples 1 to 16 do not conform to the composition of the present application. Therefore, Comparative Examples 1 to 16 had fatigue strength of 490 MPa or less and had poor fatigue durability.

TABLE 5

| Sample No. | | Concentration of TiC-based inclusion in nonmetallic inclusion (% by mass) | lattice misfit δ | transformation temperature (Af point) (° C.) | fatigue strength (MPa) |
|---|---|---|---|---|---|
| Example | 1 | 100 | 0.4238 | −5 | 540 |
| | 2 | 100 | 0.4242 | 1 | 532 |
| | 3 | 100 | 0.4248 | −3 | 526 |
| | 4 | 100 | 0.4255 | 2 | 520 |
| | 5 | 100 | 0.4259 | 17 | 513 |
| | 6 | 100 | 0.4242 | 55 | 530 |
| | 7 | 99 | 0.4248 | 3 | 518 |
| | 8 | 99.5 | 0.4252 | −12 | 523 |
| | 9 | 100 | 0.4245 | −21 | 515 |
| | 10 | 100 | 0.4238 | −4 | 525 |
| | 11 | 99.5 | 0.4255 | 52 | 515 |
| Comparative Example | 1 | 100 | <u>0.4276</u> | −5 | 452 |
| | 2 | 100 | <u>0.4232</u> | 28 | 473 |
| | 3 | 100 | <u>0.4296</u> | 5 | 490 |
| | 4 | 100 | <u>0.4296</u> | 53 | 482 |
| | 5 | <u>98.2</u> | 0.4238 | −3 | 435 |
| | 6 | <u>97.8</u> | 0.4232 | 17 | 423 |
| | 7 | 100 | <u>0.4262</u> | 5 | 475 |
| | 8 | <u>60</u> | <u>0.4225</u> | 15 | 412 |
| | 9 | <u>75</u> | <u>0.4225</u> | 3 | 415 |
| | 10 | <u>0</u> | <u>No TiC</u> | 2 | 410 |
| | 11 | 100 | <u>0.4232</u> | 52 | — |
| | 12 | <u>98.3</u> | 0.4238 | 40 | 432 |
| | 13 | 100 | 0.4265 | −1 | — |
| | 14 | <u>98</u> | 0.4255 | 3 | 442 |
| | 15 | <u>97.5</u> | 0.4235 | 90 | — |
| | 16 | 100 | <u>0.4262</u> | −20 | — |

Note:
In the table, a numerical value out of the scope of the present invention is underlined.

Next, properties of each of the samples of Examples 12 to 21 and Comparative Examples 17 to 26, that is, the lattice misfit and the fatigue strength are presented in Table 6. Wires made of the Ni—Ti-based alloy material and having a diameter of 0.5 mm (samples of Examples 12 to 21 and Comparative Examples 17 to 26) were obtained through the same step as in Examples 1 to 11 and Comparative Examples 1 to 16, except that the components presented in Table 3 (Ni, Ti, and one element or two elements (Cu and Cr (Example 21 and Comparative Example 26)) selected from the group consisting of Cu, Ta, Zr, Nb, V, Mo, Cr, Fe, and Co) were weighed, and charged into a high-frequency melting furnace to be melted to molten metal, and then the molten metal was poured into a casting template (thermoconductivity: 48 W/(m·K)) to be cast.

For all Examples 12 to 21, 100% by mass of the nonmetallic inclusion was the TiC-based inclusion having the NaCl type crystal structure and the lattice misfit of the TIC-based inclusion relative to the matrix phase in the Ni—Ti-based alloy material was 0.4238 or more and 0.4242 or less. In other words, Examples 12 to 21 conform to the composition of the present application. Therefore, Examples 12 to 21 had fatigue strength in a range of 508 to 533 MPa and excellent fatigue durability.

Meanwhile, for Comparative Examples 17 to 22, the concentration of the TIC-based inclusion in the nonmetallic inclusion was 94 to 97% by mass and the lattice misfit was 0.4262 (Comparative Example 18) or 0.4232 to 0.4235 which were out of the appropriate range of the present disclosure. For Comparative Examples 23 to 26, the lattice misfit was 0.4238 to 0.4255, but the concentration of the TiC-based inclusion in the nonmetallic inclusion was 94 to 96% by mass. In other words, Comparative Examples 17 and 19 to 22 do not conform to the composition of the present application. Therefore, Comparative Examples 17 and 19 to 22 had fatigue strength of 475 MPa or less and poor fatigue durability.

TABLE 6

| Sample No. | | TiC-based inclusion concentration (% by mass) | lattice misfit δ | fatigue strength (MPa) |
|---|---|---|---|---|
| Example | 12 | 100 | 0.4242 | 533 |
| | 13 | 100 | 0.4238 | 525 |
| | 14 | 100 | 0.4242 | 526 |
| | 15 | 100 | 0.4242 | 521 |
| | 16 | 100 | 0.4242 | 518 |
| | 17 | 100 | 0.4238 | 525 |
| | 18 | 100 | 0.4242 | 523 |
| | 19 | 100 | 0.4242 | 510 |
| | 20 | 100 | 0.4238 | 515 |
| | 21 | 100 | 0.4238 | 508 |
| Comparative Example | 17 | <u>97</u> | 0.4235 | 462 |
| | 18 | <u>96</u> | <u>0.4262</u> | 475 |
| | 19 | <u>94</u> | <u>0.4232</u> | 451 |
| | 20 | <u>95</u> | 0.4235 | 429 |
| | 21 | <u>97</u> | <u>0.4232</u> | 445 |
| | 22 | <u>95</u> | <u>0.4232</u> | 440 |
| | 23 | <u>96</u> | 0.4238 | 472 |
| | 24 | <u>95</u> | 0.4238 | 462 |
| | 25 | <u>96</u> | 0.4242 | 435 |
| | 26 | <u>94</u> | 0.4255 | 450 |

Note:
In the table, a numerical value out of the scope of the present invention is underlined.

Furthermore, when comparing Examples 12 to 21 to which one element or two elements (Cu and Cr) selected from the group consisting of Cu, Ta, Zr, Nb, V, Mo, Cr, Fe, and Co had been added with Examples 1 to 11 to which these elements had not been added, as shown in Tables 5 and 6, the presence of these elements was found to have no effect on the concentration (% by mass) of the TiC-based inclusion, the lattice misfit, and the fatigue strength. It was confirmed that the presence of these elements present in the Ni—Ti-based alloy material of the present disclosure did not have a significantly great effect on phases of the nonmetallic inclusion and physical properties.

EXPLANATION OF REFERENCE NUMERALS 1 specimen of Ni—Ti-based alloy material (sample)
2 Pt mesh electrode (counter electrode)
3 electrolytic solution
4 direct-current power supply for electrolysis
5 ice water for cooling (cooling water)
10 electrolytic extraction apparatus
11 wire made of Ni—Ti-based alloy (sample)
12 silicone oil
13 motor with revolution counter (counter)
14 power supply for heater with motor for stirrer
15 heater
16 stirrer
20 dual-drive type rotating bending fatigue tester

The invention claimed is:
1. A Ni—Ti-based alloy material comprising:
   a matrix phase consisting essentially of a Ni—Ti-based alloy and having a B2 crystal structure; and
   a nonmetallic inclusion present in the matrix phase,
      wherein
   99% by mass or more of a totality of nonmetallic inclusions is a TIC inclusion having a NaCl crystal structure, the TiC inclusion has a lattice misfit (δ) in a range of 0.4238 or more and 0.4259 or less, the lattice misfit (δ) being represented by Expression (1) below, $$\delta = (a1 - a2)/a2 \qquad \text{Expression (1)}$$

a1 is a lattice constant (Å) of the TiC inclusion and a2 is a lattice constant (Å) of the matrix phase,
the Ni—Ti-based alloy is free of $Ti_4Ni_2O_x$, and
the Ni—Ti-based alloy material has a ratio ([C]/[O] ratio) of a carbon concentration ([C]) to an oxygen concentration ([O]) in a range of 0.8 or more and less than 1.4.

2. The Ni—Ti-based alloy material according to claim 1, the Ni—Ti-based alloy material comprises 54.5% by mass or more and 57.0% by mass or less of Ni, 0.04% by mass or less of C, and 0.04% by mass or less of O, with a balance being Ti and unavoidable impurities.

3. The Ni—Ti-based alloy material according to claim 2, the Ni—Ti-based alloy material has superelasticity.

4. The Ni—Ti-based alloy material according to claim 1, the Ni—Ti-based alloy material has superelasticity.

5. The Ni—Ti-based alloy material according to claim 1, wherein 100% by mass of a totality of nonmetallic inclusions is the TIC inclusion.

6. The Ni—Ti-based alloy material according to claim 5, the Ni—Ti-based alloy material comprises 54.5% by mass or more and 57.0% by mass or less of Ni, 0.04% by mass or less of C, and 0.04% by mass or less of O, with a balance being Ti and unavoidable impurities.

7. The Ni—Ti-based alloy material according to claim 6, the Ni—Ti-based alloy material has superelasticity.

8. The Ni—Ti-based alloy material according to claim 5, the Ni—Ti-based alloy material has superelasticity.

9. A wire or a tube comprising the Ni—Ti-based alloy material according to claim 1.

10. A wire or a tube comprising the Ni—Ti-based alloy material according to claim 2.

11. A tube for a stent or for an artificial heart valve, the tube being formed of the Ni—Ti-based alloy material according to claim 4.

12. A wire for a guidewire, the wire being formed of the Ni—Ti-based alloy material according to claim 4.

13. A method for producing the Ni—Ti-based alloy material according to claim 1, the method comprising:
sequentially subjecting a Ni—Ti-based alloy raw material to at least a melting/casting step (step ), a hot working step (step 2), a cold working step (step 3), an annealing step (step 4), and a superelasticity-imparting heat treatment step (step 5), wherein
a Ni—Ti-based alloy ingot obtained in the melting/casting step (step 1) has a carbon concentration ([C]) of 0.04% by mass or less, an oxygen concentration ([O]) of 0.04% by mass or less, and a ratio ([C]/[O] ratio) of the carbon concentration ([C]) to the oxygen concentration ([O]) of 0.5 or more, and
the Ni—Ti-based alloy raw material is heated at a temperature of 500° ° C. or more and 800° C. or less in the hot working step (step 2).

14. A method for producing the Ni—Ti-based alloy material according to claim 5, the method comprising:
sequentially subjecting a Ni—Ti-based alloy raw material to at least a melting/casting step (step 1), a hot working step (step 2), a cold working step (step 3), an annealing step (step 4), and a superelasticity-imparting heat treatment step (step 5), wherein
a Ni—Ti-based alloy ingot obtained in the melting/casting step (step 1) has a carbon concentration ([C]) of 0.04% by mass or less, an oxygen concentration ([O]) of 0.04% by mass or less, and a ratio ([C]/[O] ratio) of the carbon concentration ([C]) to the oxygen concentration ([O]) of 0.5 or more, and
the Ni—Ti-based alloy raw material is heated at a temperature of 500° C. or more and 800° C. or less in the hot working step (step 2).

* * * * *